United States Patent [19]

Greig et al.

[11] Patent Number: 4,835,182

[45] Date of Patent: May 30, 1989

[54] ENHANCING DRUG DELIVERY TO THE BRAIN

[75] Inventors: Nigel H. Greig, Washington, D.C.; Daniel J. Sweeney, Indianapolis, Ind.; Stanley I. Rapoport, Washington, D.C.

[73] Assignee: The United States of America as represented by the Department of Health and Human Services, Washington, D.C.

[21] Appl. No.: 88,982

[22] Filed: Aug. 21, 1987

[51] Int. Cl.$^4$ .................. A61K 31/245; C07C 101/64
[52] U.S. Cl. ..................................... 514/538; 560/38; 560/47
[58] Field of Search .................... 560/38, 47; 574/538

[56] References Cited

FOREIGN PATENT DOCUMENTS 57-3957  4/1959  Canada ................................. 560/47
727336   3/1955  United Kingdom ................. 560/47
750155   6/1956  United Kingdom ................. 560/38

OTHER PUBLICATIONS

Greig, *Cancer Treatment Reviews*, (1984), 11, 157–186.
Greig, *Cancer Treatment Reviews*, (1987), 14, 1–28.
Greig et al., *Cancer Chemother. Pharmacol* (1988).

Afanas'eva et al., *Chemical Abstracts*, vol. 88, No. 152189y (1978).

*Primary Examiner*—Bruce D. Gray
*Attorney, Agent, or Firm*—Browdy and Neimark

[57] ABSTRACT

Tertiary butyl esters of anticancer drugs are provided which have the following formula:

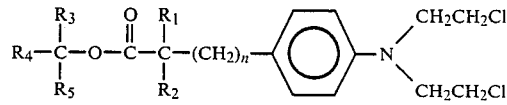

wherein $R_1$ and $R_2$ are the same or different and are selected from the group consisting of H, F, Cl, Br, and I and $R_2$ can also be $NH_2$;

$R_3$, $R_4$, and $R_5$ are the same or different and are selected from the group consisting of H, F, Cl, Br, I, and $C_1$–$C_3$ alkyl; wherein alkyl may be substituted with F, Cl, Br, or I, with the proviso that at least two of $R_3$, $R_4$, and $R_5$ are alkyl or substituted alkyl; and $n = 0$–$4$.

The compounds of the present invention can be used in treating cancer by significantly increasing the brain levels of the drugs of the invention and their active metabolites.

8 Claims, 2 Drawing Sheets

TOTAL PLASMA AND BRAIN CONCENTRATIONS (±SEM) OF COMPOUNDS POSSESSING ALKYLATING ACTIVITY FOLLOWING I.V. ADMINISTRATION OF 10 mg/kg CHLORAMBUCIL

ENHANCING DRUG DELIVERY TO THE BRAIN

FIELD OF THE INVENTION

The present invention is directed to methods for enhancing delivery of drugs to the brain by providing esters of the drugs which are brain directed.

BACKGROUND OF THE INVENTION

Melphalan and chlorambucil are two structurally related anticancer drugs that are used to treat a wide variety of malignancies. Melphalan is effective in the treatment of multiple myeloma, ovarian carcinoma, as adjuvant chemotherapy of stage II breast carcinoma, and in the regional perfusion of nonresectable melanoma. Chlorambucil is used in the treatment of chronic lymphocytic leukemia, carcinoma of the breast and ovary, and Hodgkin's and non-Hodgkin's lymphomas. Both drugs are classical bifunctional alkylating agents. Melphalan is a nitrogen mustard derivative of the large neutral amino acid L-phenylalanine, and chlorambucil is structurally similar to melphalan but lacks an amine moiety.

Unfortunately, both chlorambucil and melphalan only minimally enter the brain, which is a major site in the development of metastases, causing death. The blood-brain barrier is a significant barrier to the entry of water-soluble or ionized compounds from the bloodstream into the brain. Many pharmaceutically active compounds, do not reach the brain, where they may be most effective.

The brain is a major site in the metastatic cascade process. The incidence of metastases to the brain from the ovary, breast, and melanoma, for which melphalan and chlorambucil are administered, are approximately 5%, 10%, and 40%, respectively.

Although chlorambucil and melphalan have been used extensively in the clinic for over 20 years, it has been found that melphalan becomes hydrolyzed after administration to humans or rats to its monohydroxy and dihydroxy products, the latter having no cancer activity. Chlorambucil undergoes beta-oxidation in vivo, to yield the active metabolite phenylacetic mustard via the active intermediate 3,4-dehydro chlorambucil. However, neither of these compounds passes the blood-brain barrier. Hence, they are not useful in the treatment of brain tumors.

Speeter et al., in U.S. Pat. No. 2,821,540, disclose a method of preparing esters of 4-aminobenzoic acid which are not easily hydrolyzed in vivo. The carboxylate group of these esters is hindered by adding to at least one of the carbon atoms ortho to the carboxylate group in the 1-position of a substituent selected from the group consisting of alkyl, cycloalkyl, aralkyl, aryl, and heterocyclic radicals.

Because chlorambucil and melphalan are effective drugs for the treatment of a variety of cancers, attempts have been made to direct the drugs directly to the affected site.

Yoshida et al., in U.S. Pat. No. 4,584,136, disclose Estracyt compounds having carcinostatic agents such as chlorambucil bound thereto for transporting the active agent directly to the tumor site.

Asano et al, in U.S. Pat. No. 4,332,797, disclose chlorambucil derivatives which are obtained by chemically binding chlorambucil to an estradiol or derivative to direct the drug more specifically to cancer cells in the body.

SUMMARY OF THE INVENTION

It is an object of the present invention to overcome the above-noted deficiencies in the prior art.

It is another object of the invention to improve the treatment and survival of patients with brain tumors.

It is yet another object of the present invention to provide compounds based on chlorambucil, melphalan, phenyl propionic mustard, and phenylacetic mustard, which do not hydrolyze immediately in vivo.

It is further objection of the present invention to provide prodrugs of chlorambucil and melphalan which can readily cross the blood-brain barrier.

It is yet a further object of the present invention to produce prodrugs of chlorambucil and melphalan which can be used in cancer chemotherapy.

It has been found that tertiary butyl esters of chlorambucil, phenyl propionic mustard, phenylacetic mustard, and melphalan, can be made which, following intravenous administration, have sufficient stability in plasma and the liver to allow significant accumulation thereof in the brain. The tertiary butyl esters possess intrinsic anticancer activity, and break down to yield the anticancer agent of the parent drug. The tertiary butyl esters achieve significantly higher brain concentrations of active drug, as compared to the drugs themselves, at lower plasma drug levels.

The brain/plasma concentration ratio of active drug following equal doses of tertiary butyl chlorambucil and chlorambucil are 0.7 and 0.017 (from 5 minutes to 4 hours following drug administration), respectively, an increase of 4100%. The most widely used drug in the treatment of brain tumors is BCNU, which has a brain/plasma ratio of approximately 0.3.

The compounds of the present invention have the following formula:

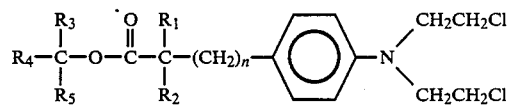

wherein
$R_1$ and $R_2$ can be the same or different, and are selected from the group consisting of H, F, Cl, Br, I; and, additionally, $R_2$ can be $NH_2$;
$R_3$, $R_4$, and $R_5$ can be the same or different and can be selected from the group consisting of H, $C_1$-$C_3$ alkyl, F, Cl, Br, I, wherein the alkyl may be substituted with F, Cl, Br, or I, with the proviso that at least two of $R_3$, $R_4$, and $R_5$ are alkyl or substituted alkyl; and
$n = 0, 1, 2, 3, 4$

DETAILED DESCRIPTION OF THE INVENTION

Figure 1:
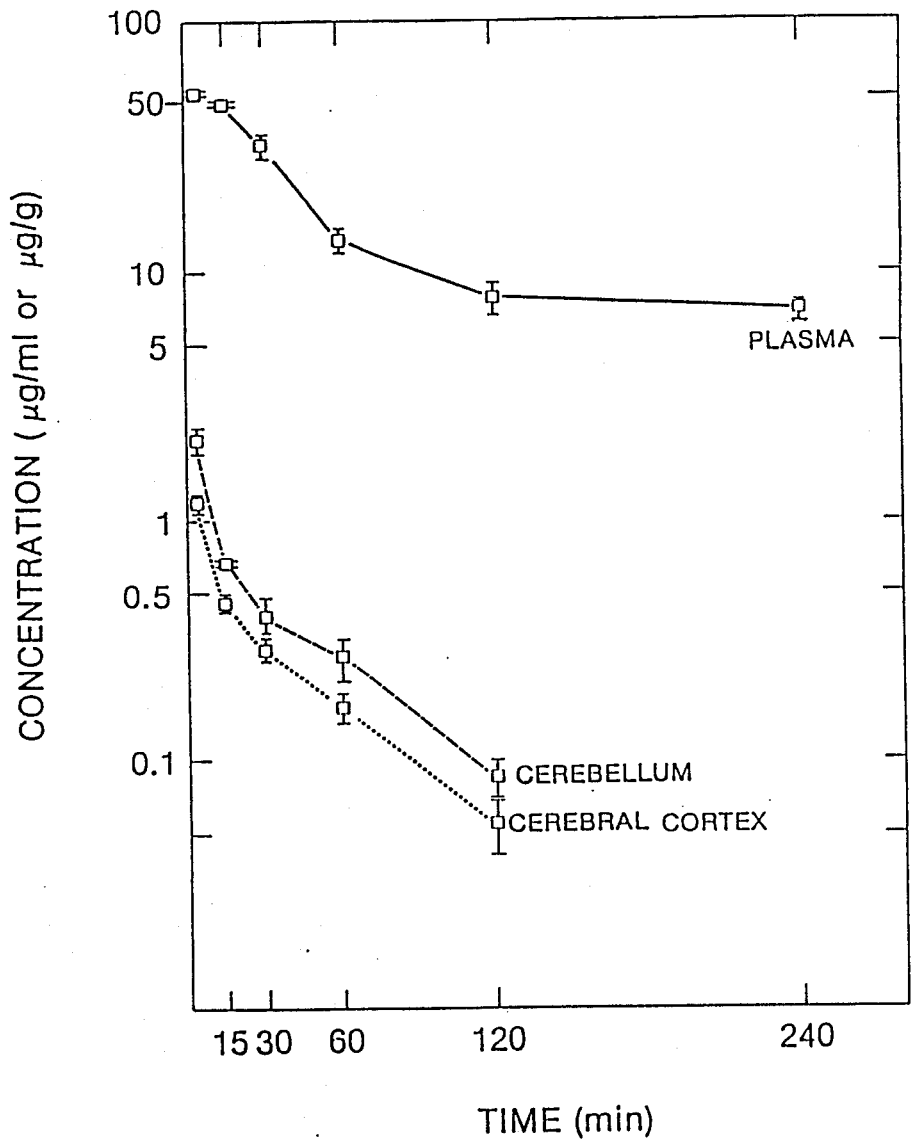
FIG. 1 shows the total plasma and brain concentrations of compounds possessing alkylating activity following intravenous administration of 10 mg/kg of chlorambucil.
Figure 2:
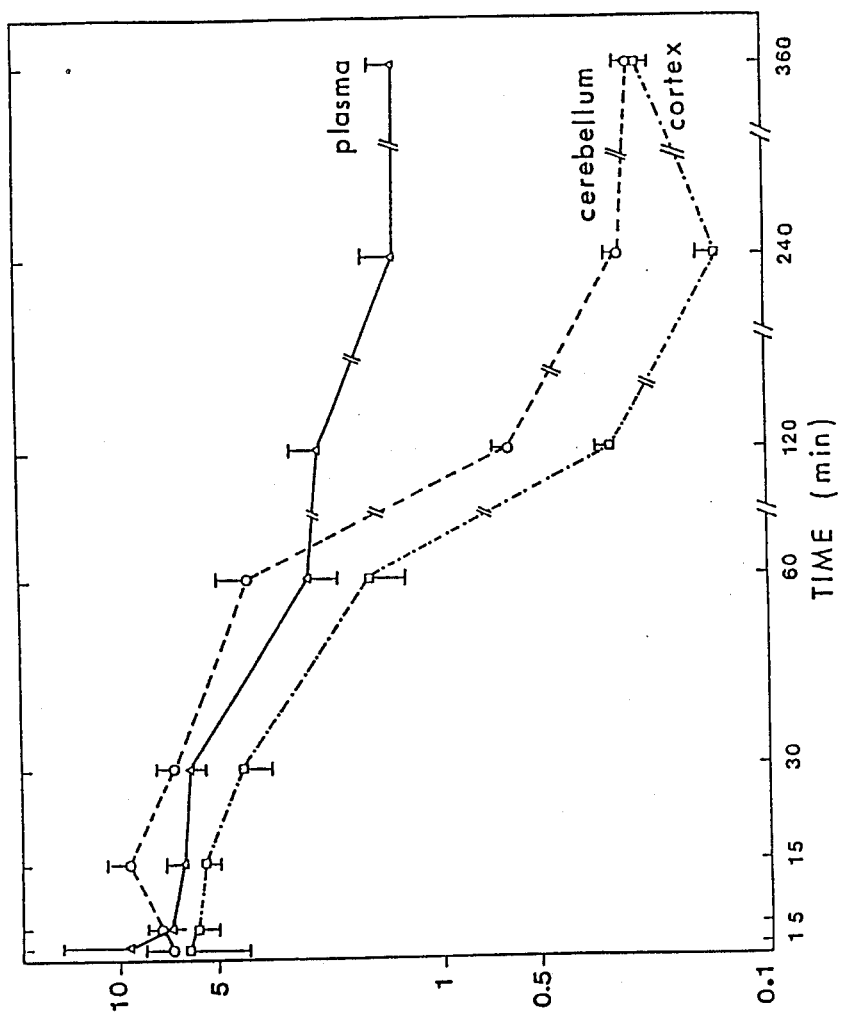
FIG. 2 shows the total concentrations of compounds possessing alkylating activity in plasma and brain following intravenous administration of tertiary butyl chlorambucil (equivalent to 10 mg/kg of chlorambucil).

The tertiary butyl esters of the present invention can be prepared from the correspondingly substituted drug and the corresponding tertiary butyl alcohol by reaction with p-toluene sulfonic acid in benzene or toluene under azeotropic conditions.

Specific base compounds which can be made more effective in crossing the blood-brain barrier according to the present invention are as follows:

CHLORAMBUCIL

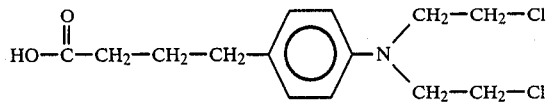

PHENYLACETIC MUSTARD

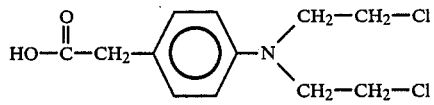

PHENYLPROPRIONIC MUSTARD

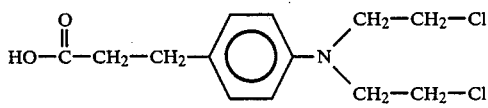

MELPHALAN

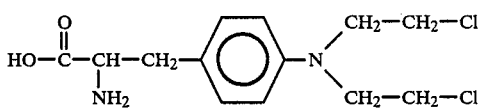

Several factors co-determine the concentration of a drug that is eventually achieved in the brain following its systemic administration and, hence, its final activity within the brain. One is the plasma concentration versus time profile of the compound and its active metabolites, which is related to its systemic metabolism and distribution. Another is the permeability of the compound and/or its active metabolites at the blood-brain barrier, which restricts the brain uptake of water soluble and ionized agents. An additional factor is the binding of the compound to plasma constituents, such as serum albumin and alpha-1-acid glycoprotein, and whether this binding is restrictive or non-restrictive for brain uptake. A final factor which is critical for lipophilic drugs is the rate of cerebral blood flow.

Following the administration of chlorambucil or melphalan to animal model or humans, significant concentrations of drug and active metabolites are found in plasma and in peripheral organs. As these agents are ionized and partially bound to plasma protein, however, only low concentrations of drug enter the brain. The mean brain/plasma concentration integral ratios of chlorambucil, phenyl acetic mustard and melphalan are 0.02, 0.01, and 0.10, respectively. Consequently, although moderate doses of these agents completely inhibit the growth of peripherally implanted tumors in animal models, similar or very high doses have little effect on the same tumor implanted within the brain. This corresponds to the relatively common development of brain metastases in patients with neoplasms whose extracerebral primaries and metastases respond to these drugs.

Chemical modification of these clinically valuable drugs, as described, produces lipophilic esters that are sufficiently stable in vivo to allow significant accumulation of active agents in the brain. The distribution of the lipophilic esters into the brain is no longer restricted by a low cerebrovacsular permeability but is dependent on blood flow which, for the brain, is high and approximately 20% of cardiac output. Hence, the brain uptake of such compounds as the tertiary butyl ester of the chlorambucil, is high and has a brain/plasma concentration integral ratio of 0.7.

Presently the prognosis of patients with malignant brain tumors is bleak, since the blood-brain barrier, although of variable integrity, severely compromises the delivery of water soluble and ionized drugs to brain tumors, which includes the majority of agents presently used clinically in cancer chemotherapy. The lipophilic nitrosoureas, whose brain uptakes are not restricted by the blood-brain barrier, are amongst the very few agents that have demonstrated activity against brain tumors. Several studies have demonstrated that the nitroureas are not cross resistant with classical bifunctional alkylating agents. Drugs such as chlorambucil, phenlacetic mustard and melphalan, modified as described, have the necessary properties for brain tumor chemotherapy.

The compounds of the present invention can be administered to patients suffering from cancer at doses ranging from about 0.2-10 mg/day total dosage. The drugs may be administered through the carotid artery to reduce the dosage required. Oral administration of the drugs requires a greater dosage than intravenous administration. However, higher concentrations, up to 250 mg/day, may be administered if combined with autologous bone marrow rescue.

The compounds of the present invention can be combined with a pharmaceutically acceptable carrier therefore, and optionally other therapeutic and/or prophylactic ingredients. The carriers must be "acceptable" in the sense of being compatible with the other ingredients of the formula and not deleterious to the recipient thereof.

The dosage of the compounds is such as to provide from about 0.2 to about 20 mg/day total dosage of active ingredient.

Pharmaceutical formulations suitable for oral administration wherein the carrier is a solid are most preferably presented as unit dose formulations such as boluses, capsules. Sachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, interdiluent, lubricating, surface active or dispersing agent. Moulded tablets may be made by moulding an inert liquid diluent. Tablets may be optionally coated and, if uncoated, may optionally be scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Pharmaceutical formulations suitable for oral administration wherein the carrier is a liquid may conveniently be presented as a solution in an aqueous liquid or a non-aqueous liquid, or as an oil-in-water or water-in-oil liquid emulsion. Pharmaceutical formulations suitable for parenteral administration are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The pharmaceutical formulations may be any formulation in which the active compound may be administered and include those suitable for oral or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

The foregoing description of the specific embodiments will so fully reveal the general nature of the invention that others can, by applying current knowledge, readily modify and/or adapt for various applications such specific embodiments without departing from the generic concept, and therefor such adaptations and modifications are intended to be comprehended within the meaning and range of equivalents of the disclosed embodiments. It is to be understood that the phraseology or terminology employed herein is for the purpose of description and not of limitation.

What is claimed is:

1. A compound having the following formula:

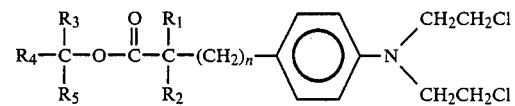

wherein $R_1$ and $R_2$ are the same or different and are selected from the group consisting of H, Cl, F, Br, I and $R_2$ may also be $NH_2$;

$R_3$, $R_4$, and $R_5$ are the same or different and are selected from the group consisting of $C_1$–$C_3$ alkyl, H, F, Cl, Br, I; wherein alkyl may be substituted with F, Cl, Br, or I, with the proviso that at least two of $R_3$, $R_4$ and $R_5$ are alkyl or substituted alkyl; and n is an integer of 0–4.

2. A method of treating cancer comprising administering to a patient suffering from cancer an effective amount of a compound of claim 1.

3. The method of claim 2 wherein the compound is tertiary-butyl chlorambucil.

4. The method of claim 2 wherein the compound is administered through the carotid artery.

5. A method of administering chlorambucil across the blood-brain barrier comprising administering to a patient in need of chlorambucil a compound of claim 1 wherein n is 2.

6. A method of administering to a patient in need of melphalan a compound of claim 1 wherein n is 1.

7. The method of claim 5 wherein the compound is tertiary-butyl chlorambucil.

8. The method of claim 6 wherein the compound is tertiary-butyl melphalan.

* * * * *

REEXAMINATION CERTIFICATE (1586th)
United States Patent [19]
Greig et al.

[11] B1 4,835,182

[45] Certificate Issued Nov. 5, 1991

[54] ENHANCING DRUG DELIVERY TO THE BRAIN

[75] Inventors: Nigel H. Greig, Washington, D.C.; Daniel J. Sweeney, Indianapolis, Ind.; Stanley I. Rapoport, Washington, D.C.

[73] Assignee: The United States of America as represented by the Department of Health and Human Services, Washington, D.C.

Reexamination Request:
No. 90/002,048, Jun. 8, 1990

Reexamination Certificate for:
Patent No.: 4,835,182
Issued: May 30, 1989
Appl. No.: 88,982
Filed: Aug. 21, 1987

[51] Int. Cl.$^5$ ............ A61K 31/245; C07C 101/64; C07C 229/00
[52] U.S. Cl. ............................ 514/538; 560/38; 560/47
[58] Field of Search .................. 514/538; 560/38, 47

[56] References Cited

PUBLICATIONS

Roehrig et al., "Synthesis and Antitumor Activity of 4-(p-(Bis(2-chloroethyl)amino)phenyl)butyrates", Journal of Pharmaceutical Sciences, vol. 69, No. 10, Oct. 1980, pp. 1232-1234.

*Primary Examiner*—Bruce D. Gray

[57] ABSTRACT

Tertiary butyl esters of anticancer drugs are provided which have the following formula:

wherein $R_1$ and $R_2$ are the same or different and are selected from the group consisting of H, F, Cl, Br, and I and $R_2$ can also be $NH_2$;

$R_3$, $R_4$, and $R_5$ are the same or different and are selected from the group consisting of H, F, Cl, Br, I, and $C_1$-$C_3$ alkyl; wherein alkyl may be substituted with F, Cl, Br, or I, with the proviso that at least two of $R_3$, $R_4$, and $R_5$ are alkyl or substituted alkyl; and $n = 0$-4.

The compounds of the present invention can be used in treating cancer by significantly increasing the brain levels of the drugs of the invention and their active metabolites.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5 and 6 are cancelled.

Claims 1 and 2 are determined to be patentable as amended.

Claims 3, 4, 7 and 8, dependent on an amended claim, are determined to be patentable.

New claims 9, 10, 11, 12 and 13 are added and determined to be patentable.

1. A compound having the following formula:

wherein
- $R_1$ and $R_2$ are the same or different and are selected from the group consisting of H, Cl, F, Br, I and $R_2$ may also be $NH_2$;
- $R_3$, $R_4$, and $R_5$ are the same or different and are selected from the group consisting of $C_1$-$C_3$ alkyl, [H, F, Cl, Br, I]; wherein alkyl may be substituted with F, Cl, Br, or I, [with the proviso that at least two of $R_3$, $R_4$ and $R_5$ are alkyl or substituted alkyl]; and
- n is an integer of 0-4.

2. A method of treating cancer comprising administering to a patient suffering from cancer an effective amount of a compound [of claim 1] *having the following formula:*

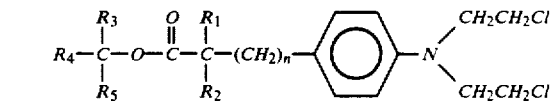

*wherein*
- $R_1$ *and* $R_2$ *are the same or different and are selected from the group consisting of H, Cl, F, Br, I and* $R_2$ *may also be* $NH_2$;
- $R_3$, $R_4$, *and* $R_5$ *are the same or different and are selected from the group consisting of* $C_1$-$C_3$ *alkyl; wherein alkyl may be substituted with F, Cl, Br, or I; and*
- *n is an integer of 0-4.*

9. *A pharmaceutical composition comprising an effective amount of the compound of claim 1, and a pharmaceutically acceptable carrier.*

10. *The compound according to claim 1 wherein* $R_1$ *and* $R_2$ *are hydrogen;* $R_3$, $R_4$, *and* $R_5$ *are methyl; and n is 2.*

11. *A method of treating a brain tumor which comprises administering to a patient suffering from a brain tumor an effective amount of the compound having the following formula:*

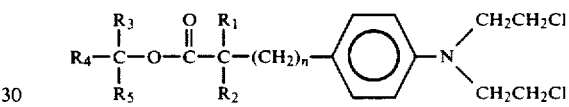

*wherein*
- $R_1$ *and* $R_2$ *are the same or different and are selected from the group consisting of H, Cl, F, Br, I and* $R_2$ *may also be* $NH_2$;
- $R_3$, $R_4$, *and* $R_5$ *are the same or different and are selected from the group consisting of* $C_1$-$C_3$ *alkyl; wherein said alkyl may be substituted with F, Cl, Br, or I; and*
- *n is an integer of 0-4.*

12. *A method of treating a brain tumor which comprises administering to a patient suffering from a brain tumor an effective amount of the compound having the formula:*

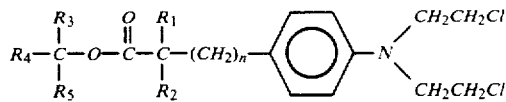

*wherein* $R_1$ *and* $R_2$ *are hydrogen;* $R_3$, $R_4$ *and* $R_5$ *are methyl; and n is 2.*

13. *A pharmaceutical composition which comprises an effective amount of the compound according to claim 10, and a pharmaceutically acceptable carrier.*

* * * * *